US00PP10106P

United States Patent [19]

Jacobsen

[11] Patent Number: Plant 10,106

[45] Date of Patent: Nov. 4, 1997

[54] POINSETTIA PLANT 'PETERSTAR JINGLE BELLS'

[75] Inventor: Peter Jacobsen, deceased, late of Skibby, Denmark, by Aase Jacobsen, executrix

[73] Assignee: Paul Ecke Ranch, Inc., Encinitas, Calif.

[21] Appl. No.: 630,134

[22] Filed: Apr. 10, 1996

[51] Int. Cl.[6] ..... A01H 5/00

[52] U.S. Cl. ..... Plt./86.1

[58] Field of Search ..... Plt./86.1

[56] References Cited

U.S. PATENT DOCUMENTS

P.P. 9,315 10/1995 Zerr ..... Plt./86.1

P.P. 9,316 10/1995 Zerr ..... Plt./86.1

P.P. 9,685 11/1996 Bevelander ..... Plt./86.1

*Primary Examiner*—James R. Feyrer

*Attorney, Agent, or Firm*—Arnold, White & Durkee

[57] ABSTRACT

Poinsettia 'Peterstar Jingle Bells' is a new cultivar, distinguished by bicolored red with pink splotched bracts, large flowers, strong stems and self-branching characteristics. 'Peterstar Jingle Bells' is a sport of the red bracted 'Peterstar' (U.S. Plant Pat. No. 8,259) with the same flowering response and cultural requirement. The new plant produces a very desirable branched flowering pot plant. The new plant is resistant to epinasty after being confined to shipping containers. The post-production foliage and bract retention are good.

1 Drawing Sheet

BACKGROUND OF THE NEW PLANT

This new poinsettia cultivar originated as a bicolored pink on red bracted sport of 'Peterstar' (U.S. Plant Pat. No. 8,259) in my greenhouse in Skibby, Denmark in 1993. It was induced through irradiation of vegetative plants with 2500 rads of γ radiation, and was selected from about 200 mutants so produced, because of its bicolored pink on red bracts, large flowers, strong stems, self branching, and dark green leaves, traits which help distinguish it from other poinsettia cultivars, and seemed to make it a desirable plant for commercial greenhouse production. 'Peterstar Jingle Bells' differed from its parent 'Peterstar' in having bicolored red with pink flecked bracts as compared to the bright red bracts of 'Peterstar', two distinct bract coloration patterns exist among bi-color poinsettias. Some like 'Peterstar Jingle Bells' have red bracts with irregularly shaped areas of pink or white randomly scattered over the bract surface. Others have pink bracts with white margins of various widths. Poinsettias 'Fispue' (U.S. Plant Pat. No. 9,351), 'Fisbla' (U.S. Plant Pat. No. 9,316), 'Marble Star' (U.S. Plant Pat. No. 9,685) and 'Peterstar Jingle Bells' (U.S. Plant Pat. No. 9,877), are sports of 'Peterstar' (U.S. Plant Pat. No. 8,259) and have pink bracts with white margins of various widths. 'Peterstar Jingle Bells' resembles poinsettia '8-84' (U.S. Plant Pat. No. 7,230) but distinctly differs in the following traits. 'Peterstar Jingle Bells' has a more compact growth habit and flowers earlier. After selection, 'Peterstar Jingle Bells' was vegetatively reproduced from stem cuttings for test purposes in Encinitas, Calif. By subjecting clones of this plant to successive generations of vegetative propagation, it was demonstrated that the distinctive characteristics of 'Peterstar Jingle Bells' held true from generation to generation. Grown under the same greenhouse environment, 'Peterstar Jingle Bells' had the same growth habit and flowering response time as the parent plant 'Peterstar'.

DESCRIPTION OF THE PHOTOGRAPHS

Poinsettia 'Peterstar Jingle Bells' is illustrated in the accompanying color photographs.

The upper photo is a side view of one branched plant in full flower.

The lower photo is a top view of the same plant showing flower and bract formation.

DESCRIPTION OF THE PLANT

The following is a detailed description of this new poinsettia as observed in Encinitas, Calif., USA during December 1995. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between 'Peterstar Jingle Bells' and poinsettia '8-84'.

| Plant | 'Peterstar Jingle Bells' | '8-84' |
|---|---|---|
| Flower Response | 8.5 weeks | 10 weeks |
| Blooming date (Northern hemisphere) | November 25 | December 5 |
| Bract color | RHS 45A-46B (red)<br>RHS 52B (pink) | RHS 46A-B (red)<br>RHS 51B (pink) |

Origin: Sport of 'Peterstar' (U.S. Plant Pat. No. 8,259), induced through irradiation of vegetative plants with 2500 rads of γ radiation.

Classification:

*Botanical.*—*Euphorbia pulcherrima* Willd.

*Common name.*—Poinsettia.

*Cultivar name.*—'Peterstar Jingle Bells'.

Form: Shrub.

Height: Medium.

Internode length: the internode length on flowering branches is approximately 1.3 cm.

Growth habit: As a single stemmed plant, upright and vigorous with self-branching side shoots. The application of a chemical growth retardant may not be needed to restrict height for commercial pot plant production. I observed one pinched plant in a pot with an overall height of 38 cm and an overall width of 41 cm. The bract diameter of individual flowers was 28 cm.

Branching: Axillary branches will develop and terminate in a flower without pinching. However, it is usually desirable to pinch 'Peterstar Jingle Bells' before flower induction and remove all terminal dominance. Then, all axillary branches will develop uniformly and at a faster rate.

Growth rate: Rooting of stem cutting occurs in 12–18 days under intermittent mist and rooting medium temperatures of 21°–22° C.

Flowering: The plant will flower in eight to nine weeks under continuous long night conditions and night temperatures of about 16°–18° C. Like its parent, 'Peterstar'), 'Peterstar Jingle Bells' will be in full bloom in late November in the northern hemisphere under natural day-length conditions.

Foliage: The foliage was clean and uniformly dark green from bottom to top of the plant. The leaves were of medium size, leaf blades typically being 13–14 cm long and 7–8 cm wide with leaf petioles 4–5 cm long.

*Leaf shape.*—Typical leaves are ovate to lanceolate with acute to obtuse bases and acuminate tips. Leaf margins are mostly entire.

*Leaf surface.*—The upper surface is slightly rugose and glabrous and the under surface is finely pubescent.

*Color.*—Upper side — Green, darker than R.H.S. 147A. Under side — Green, near R.H.S. 147B.

*Retention.*—The foliage retention is good even under low light intensities in the consumer's home.

Bracts: Generally there were 17–21 bicolored pink on red bracts of various sizes subtending the cyathia. The primary bracts had blades typically 14–15 cm long and 8–9 cm wide with petioles about 2 cm long.

*Shape.*—Primary bracts are ovate with acute bases and acuminate tips. Margins are entire. Secondary bracts are elliptic and have entire margins.

*Surface.*—The bract surface is slightly rugose.

*Color.*—Upper side — Bicolored: Dark red bracts with irregularly shaped pink splotches. Red color R.H.S. 45A-46B. Pink color near R.H.S. 52B. Fewer and generally smaller light pink splotches, near R.H.S. 52D, also appear randomly and sometimes along the bract margins. Under side — Bicolored: Red with pink splotches. The patterns of each color mostly mirror the upper surface. The red is near R.H.S. 46C and the pink is near R.H.S. 52D.

Flowers: Generally, 18–22 cyathia (flowers) were present when the plant was in full bloom. Each cyathium is about 5 mm long and 4 mm wide, green in color, and fringed red at the distal end. Usually one, but occasionally two yellow nectar cups protrude from the side of each cyathium. The flower pedicel is also green and about 5 mm in length. The stamens protruding from the cyathia are red. The stigmas are red and trifurcate. Cyathia retention was about three weeks beyond the time the flower was fully mature.

*Nectar exudate.*—Present, abundant.

*Seed formation.*—Self-incompatible.

*Fertility.*—Not observed.

Post production: 'Peterstar Jingle Bells' was resistant to epinasty after being confined to shipping containers. The foliage and bract retention were good.

What is claimed is:

1. A new and distinct Poinsettia plant, substantially as herein shown and described, distinguished by its strong stems, bicolored red with pink splotched bracts, self branching, large flowers, good cyathia development and good leaf and bract retention in the consumer environment.

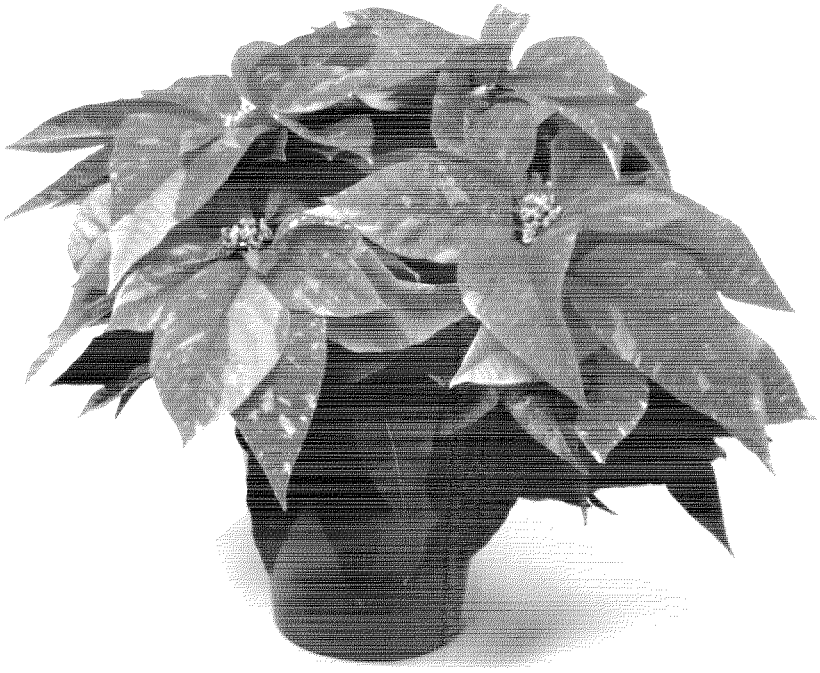
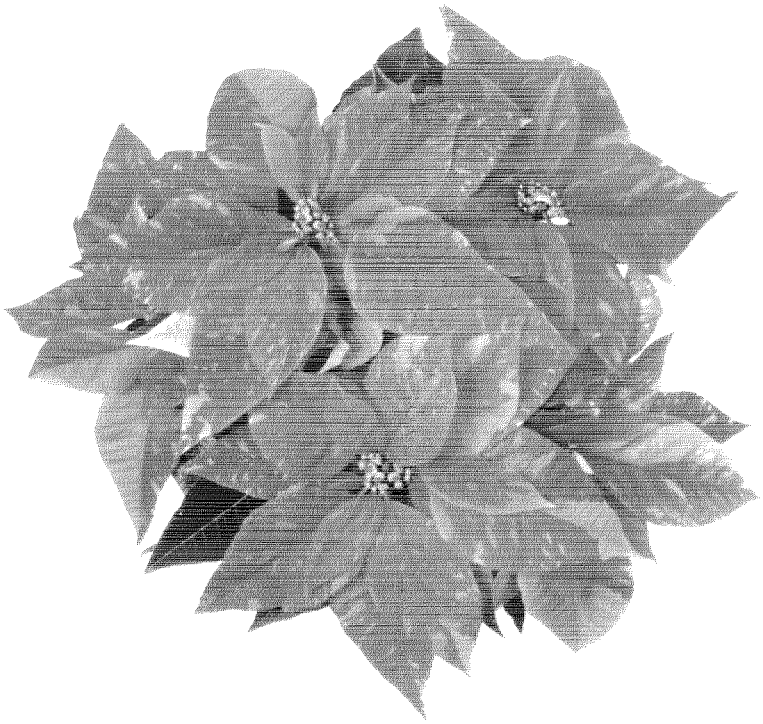

* * * * *